(12) United States Patent
Guegler et al.

(10) Patent No.: US 6,730,505 B2
(45) Date of Patent: May 4, 2004

(54) ISOLATED HUMAN DRUG-METABOLIZING PROTEINS, NUCLEIC ACID MOLECULES ENCODING HUMAN DRUG-METABOLIZING PROTEINS, AND USES THEREOF

(75) Inventors: Karl Guegler, Menlo Park, CA (US); Karen A. Ketchum, Germantown, MD (US); Valentina Di Francesco, Rockville, MD (US); Ellen M. Beasley, Darnestown, MD (US)

(73) Assignee: Applera Corporation, Norwalk, CT (US)

(*) Notice: Subject to any disclaimer, the term of this patent is extended or adjusted under 35 U.S.C. 154(b) by 13 days.

(21) Appl. No.: 10/162,639

(22) Filed: Jun. 6, 2002

(65) Prior Publication Data

US 2003/0166187 A1 Sep. 4, 2003

Related U.S. Application Data

(62) Division of application No. 09/735,935, filed on Dec. 14, 2000, now Pat. No. 6,420,150.
(60) Provisional application No. 60/252,895, filed on Nov. 27, 2000.

(51) Int. Cl.⁷ .................................................. C12N 9/10
(52) U.S. Cl. ....................................................... 435/193
(58) Field of Search ........................................ 435/193

(56) References Cited

FOREIGN PATENT DOCUMENTS

EP       0 943 688 A       9/1999
WO       WO 99/22005 A     5/1999

OTHER PUBLICATIONS

Habuchi, H., et al. (1998) J. Biol. Chem. 273(15), 9208–9213.*
George, E., et al. (1970) Clin. Chim. Acta 30, 317–324.*
Humphries, D.E., et al. (1997) Biochem. J. 325, 351–357.*
Humphries, D.E., et a. (1998) Biochem. J. 332, 303–307.*
Schworak, N. et al: "Molecular Cloning and Expression of Mouse and Human cDNAs Encoding Heparan Sulfate D–Glucosaminyl 3–O–Sulfotransferase" Journal of Biological Chemistry, vol. 272 (Oct. 31, 1997), pp. 28008–28019, XP002216445.
Habuchi, O.: "Diversity and functions of glycosaminoglycan sulfotransferases" Biochimica et Biophysica Acta, vol. 1474 (2000), pp. 115–127, XP004276547.

* cited by examiner

Primary Examiner—Charles L. Patterson, Jr.
(74) Attorney, Agent, or Firm—Celera Genomics; Lin Sun-Hoffman

(57) ABSTRACT

The present invention provides amino acid sequences of peptides that are encoded by genes within the human genome, the drug-metabolizing enzyme peptides of the present invention. The present invention specifically provides isolated peptide and nucleic acid molecules, methods of identifying orthologs and paralogs of the drug-metabolizing enzyme peptides, and methods of identifying modulators of the drug-metabolizing enzyme peptides.

6 Claims, 8 Drawing Sheets cDNA sequence:
```
  1 ATGAGCTTAA AGTGTCTCTG TCTTGCTTGC AGGCTACAAC CCATTTGCCC
 51 CATTGAAGGT CGACTGGGTG GAGCCCGCAC TCAGGCTGAA TTCCCACTTC
101 GCGCCCTGCA GTTTAAGCGT GGCCTGCTGC ACGAGTTCCG GAAGGGCAAC
151 GCTTCCAAGG AGCAGGTTCG CCTCCATGAC CTGGTCCAGC AGCTCCCCAA
201 GGCCATTATC ATTGGGGTGA GGAAAGGAGG CACAAGGGCC CTGCTTGAAA
251 TGCTGAACCT ACATCCGGCA GTAGTCAAAG CCTCTCAAGA AATCCACTTT
301 TTTGATAATG ATGAGAATTA TGGTAAGGGC ATTGAGTGGT ATAGGAAAAA
351 GATGCCTTTT TCCTACCCTC AGCAAATCAC AATTGAAAAG AGCCCAGCAT
401 ATTTTATCAC AGAGGAGGTT CCAGAAAGGA TTTACAAAAT GAACTCATCC
451 ATCAAGTTGT TGATCATTGT CAGGGAGCCA ACCACAAGAG CTATTTCTGA
501 TTATACTCAG GTGCTAGAGG GGAAGGAGAG GAAGAACAAA ACTTATTACA
551 AGTTTGAGAA GCTGGCCATA GACCCTAATA CATGCGAAGT GAACACAAAA
601 TACAAAGCAG TAAGAACCAG CATCTACACC AAACATCTGG AAAGGTGGTT
651 GAAATACTTT CCAATTGAGC AATTTCATGT CGTCGATGGA GATCGCCTCA
701 TCACGGAACC TCTGCCAGAA CTTCAGCTCG TGGAGAAGTT CCTAAATCTG
751 CCTCCAAGGA TAAGTCAATA CAATTTATAC TTCAATGCTA CCAGAGGGTT
801 TTACTGCTTG CGGTTTAATA TTATCTTTAA TAAGTGCCTG GCGGGCAGCA
851 AGGGGCGCAT TCATCCAGAG GTGGACCCCT CTGTCATTAC TAAATTGCGC
901 AAATTCTTTC ATCCTTTTAA TCAAAAATTT TACCAGATCA CTGGGAGGAC
951 ATTGAACTGG CCCTAAGGGC (SEQ ID NO:1)
```

FEATURES:
5'UTR:
Start Codon: 1
Stop Codon: 964
3'UTR: 967

HOMOLOGOUS PROTEIN:
Top 10 BLAST Hits:
```
gi|4826764|ref|NP_005105.1| heparan sulfate (glucosamine) 3-O-s...    303  1e-81
gi|6754246|ref|NP_034604.1| heparan sulfate (glucosamine) 3-O-s...    297  1e-79
gi|9957244|gb|AAG09283.1| (AF177430) 3-O-sulfotransferase [Ratt...    293  3e-78
gi|7293568|gb|AAF48941.1| (AE003511) CG7890 gene product [Droso...    251  7e-66
gi|5174463|ref|NP_006034.1| heparan sulfate (glucosamine) 3-O-s...    248  6e-65
gi|5174467|ref|NP_006032.1| heparan sulfate (glucosamine) 3-O-s...    247  1e-64
gi|5174465|ref|NP_006033.1| heparan sulfate (glucosamine) 3-O-s...    247  1e-64
gi|9055264|ref|NP_061275.1| D-glycosaminyl 3-O-sulfotransferase...    240  2e-62
gi|4835727|gb|AAD30210.1|AF105378_1 (AF105378) heparan sulfate ...    235  6e-61
gi|7503118|pir||T33493 hypothetical protein F40H3.5 - Caenorhab...    187  2e-46
```

EST:
```
gi|6990086 /dataset=dbest /taxon=960...                                672  0.0
gi|5362532 /dataset=dbest /taxon=9606 ...                              660  0.0
gi|4682357 /dataset=dbest /taxon=9606 ...                              571  e-161
```

FIGURE 1A

EXPRESSION INFORMATION FOR MODULATORY USE:
gi|6990086 / lung
gi|5362532 / lung carcinoid
gi|4682357 /lung carcinoid Tissue expression
Human Brain
Human bone marrow
Human colon
Human fetal brain
Human fetal heart
Human fetal liver
Human fetal lung
Human pancreas
Human placenta

FIGURE 1B

```
  1 MSLKCLCLAC RLQPICPIEG RLGGARTQAE FPLRALQFKR GLLHEFRKGN
 51 ASKEQVRLHD LVQQLPKAII IGVRKGGTRA LLEMLNLHPA VVKASQEIHF
101 FDNDENYGKG IEWYRKKMPF SYPQQITIEK SPAYFITEEV PERIYKMNSS
151 IKLLIIVREP TTRAISDYTQ VLEGKERKNK TYYKFEKLAI DPNTCEVNTK
201 YKAVRTSIYT KHLERWLKYF PIEQFHVVDG DRLITEPLPE LQLVEKFLNL
251 PPRISQYNLY FNATRGFYCL RFNIIFNKCL AGSKGRIHPE VDPSVITKLR
301 KFFHPFNQKF YQITGRTLNW P (SEQ ID NO:2)
```

FEATURES:
Functional domains and key regions:
Prosite results:

[1] PDOC00001 PS00001 ASN_GLYCOSYLATION
N-glycosylation site

Number of matches: 4
```
      1    50-53  NASK
      2   148-151 NSSI
      3   179-182 NKTY
      4   262-265 NATR
```
---

[2] PDOC00005 PS00005 PKC_PHOSPHO_SITE
Protein kinase C phosphorylation site

Number of matches: 4
```
      1     2-4   SLK
      2   150-152 SIK
      3   161-163 TTR
      4   314-316 TGR
```
---

[3] PDOC00006 PS00006 CK2_PHOSPHO_SITE
Casein kinase II phosphorylation site

```
          27-30  TQAE
```
---

[4] PDOC00008 PS00008 MYRISTYL
N-myristoylation site

Number of matches: 3
```
      1    23-28  GGARTQ
      2    72-77  GVRKGG
      3    76-81  GGTRAL
```

FIGURE 2A

BLAST Alignment to Top Hit:

Score = 774 (277.5 bits), Expect = 6.0e-76, P = 6.0e-76
Identities = 137/258 (53%), Positives = 189/258 (73%), Frame = +2
>TRM|O14792|O14792 /def="HEPARAN SULFATE 3-O-SULFOTRANSFERASE-1 PRECURSOR. "
    /org=Homo_sapiens /date=01-MAY-2000 /mol_type=PRT /len=307
    /gene_name=3OST /mol_weight=35773 /seq_status=PRELIMINARY
    Length = 307

```
Query:    191 QQLPKAIIIGVRKGGTRALLEMLNLHPAVVKASQEIHFFDNDENYGKGIEWYRKKMPFSY 370
              QQLP+ IIIGVRKGGTRALLEML+LHP V A E+HFFD +E+Y G+ WY +MPFS+
Sbjct:     52 QQLPQTIIIGVRKGGTRALLEMLSLHPDVAAAENEVHFFDWEEHYSHGLGWYLSQMPFSW 111

Query:    371 PQQITIEKSPAYFITEEVPERIYKMNSSIKLLIIVREPTTRAISDYTQVLEGKERKNKTY 550
              P Q+T+EK+PAYF + +VPER+Y MN SI+LL+I+R+P+ R +SDYTQV    +K+K Y
Sbjct:    112 PHQLTVEKTPAYFTSPKVPERVYSMNPSIRLLLILRDPSERVLSDYTQVFYNHMQKHKPY 171

Query:    551 YKFEKLAIDPNTCEVNTKYKAVRTSIYTKHLERWLKYFPIEQFHVVDGDRLITEPLPELQ 730
                  E+ +    +N YKA+  S+Y H++ WL++FP+    H+VDGDRLI +P PE+Q
Sbjct:    172 PSIEEFLVRDG--RLNVDYKALNRSLYHVHMQNWLRFFPLRHIHIVDGDRLIRDPFPEIQ 229

Query:    731 LVEKFLNLPPRISQYNLYFNATRGFYCLRFNIIFNKCLAGSKGRIHPEVDPSVITKLRKF 910
              VE+FL L P+I+  N YFN T+GFYCLR +   ++CL  SKGR HP+VDP ++ KL ++
Sbjct:    230 KVERFLKLSPQINASNFYFNKTKGFYCLR-DSGRDRCLHESKGRAHPQVDPKLLNKLHEY 288

Query:    911 FHPFNQKFYQITGRTLNW 964
              FH  N+KF+++ GRT +W
Sbjct:    289 FHEPNKKFFELVGRTFDW 306 (SEQ ID NO:4)
```

Hmmer search results (Pfam):
Scores for sequence family classification (score includes all domains):
Model     Description                                    Score    E-value  N
--------  -----------                                    -----    -------  ---
PF02004   Protein of unknown function                    4.3      6.5      1

Parsed for domains:
Model     Domain  seq-f  seq-t   hmm-f  hmm-t    score   E-value
--------  ------  -----  -----   -----  -----    -----   -------
PF02004   1/1     133    147 ..  266    280  .]   4.3     6.5

FIGURE 2B

```
   1 ATTAGCTTCC AATCATTTAC CTTTTACTTA GTAATTGATC TAATGATCAC
  51 TAATGCATTA TTATTTAGTT GATGATTCTT TTCATTTTTT TAACTCTGTC
 101 TCTAGTCTCT AAGGGGATAG CTTTTATTTG GAATTGAATT GTTTGGTGGG
 151 CTTTCTAAAA GCCTCTCACT TCAGACTTTG AGATTATGTC TGAAGGTAAC
 201 AGGCTTATTT AGGCCCACTC TCCAGTAACT GAAGACCCTG CTTTCTGGGA
 251 GGGAGACAGA GGTTACTTCT ACCATCCCTT CCAATCCTAA ACCTGTATGA
 301 TTTTTCAGTC TGGGACCCAT ACTCAGAATC CATGCTTTCA GAAGTGGGAA
 351 AGAATATGAT ATTTTCTCAA ATTTTCACAT TCTATCTTGA GTTAGGGAGT
 401 CCAAAAAGCG ACTATTCTGC AGGATGTGAT CTCCCAGGGT AGAAGATAGA
 451 AAGAGGAAGG AAGTAAAGAA GGAAAATGAC CCTTTCTACA AGTGGGGAAA
 501 TTCCATTTGA CCTCAAACAA AGCAGAGACT GTCTATATCA GCCACTCTCA
 551 GCCAGGGTAC TATGAAAGAA TTAAATCCTA CAAAAAAGAA TTTGAGTGAC
 601 TGTTTCCTCA ATTCTTCCAA GGATGGTACT AGCATCATTC TAGGTGCTTA
 651 GGACAGAAAT CCATCAATGG ATGCCTTATG GAATTAGAGC TTAATTCTCA
 701 ACCAGAACCC AAGAAGAACT GAAAGATGAA CTTGTATTAT TCCAATCAGT
 751 GTCACAATTA AAAGCATCTT TGCCTATGTA TCTATTGATA ATTTTACATC
 801 CTCCATTTAA AGCCCTAGTA CATTAATCTC ATTAACAAAT TTATAAAAAC
 851 AAAATTCATG TTTCTCTAAA CTATTAACCG GGTTAAATCC TGTTTTTTAA
 901 AAGCTGTCTA GGCCAGGCAC AGTAGCTCAC GCCTGTAATC CCAGCACTTT
 951 GGGAGGCTGA GGCAGGCGAA TCACGAGATC AGGAGTTCAA GACCAGCCAG
1001 GCCAACATGG TGAAACCTTG TCTCTACTAA AAATACAAAA ATTAGCTGGG
1051 TATGGTGGCG CAGGCCTGTA ATCCCAGCTA CTCGGGAGGC TGAGGCAGGA
1101 GAATCTCTTG AACCCAGGAG ACAGAGATTG CAGTGAGCCA AGATCGTGCC
1151 ACTGCACTGC AGCCTAGGCA ACAGACCAAG ACTCCGTCTC AAAAAAAAAA
1201 GAAAAAAAAG TTGTCTATAT TTTCACACTT TCCACAATGA GCATGAGTTG
1251 TTTTAAAAAT CATAAAAAAG AAACATCGTG AAAAGTAGTA TACATTGATA
1301 TTTTTCCTTA AGCATTATGA TAGATAGCTG TTTAAACAGA ACAAAGACCA
1351 AGACCATGCT CCTCAATTCT GCAGAACAGG CTGAGTGTAT TAGTCCGTTT
1401 TCACAGTGCT ATAAAGACAT ACCTGAGACT GAGTAATTTA TAAAGAAAAA
1451 AGGTTTAATT GACACACAGT TCTGCATGGC TGGGGAAGCC TCAGAAAACT
1501 TACAATCATG GCAGAAGGCA AAGAAGAAGC AAGGCACGTC TTACTTGGTG
1551 GCAGGAGAGA GAGGGAGCTT GCAGGGGGCG GTGCCACACA GTTTTAAACC
1601 ATCAAATCTC ATGAGAACTC ACTATCATGA AAACAAGGGG TAAATACACC
1651 CCCATAATCC AGTCACCTCC CACCAAGCCC CTCCTCCGAC ATGTGGGGAT
1701 TACAATTCGG GATGAGATTT GGGTGGGGGC ACAGAGCCAA ACCATATCAC
1751 TGGGCATGAC CTTGAGGTTG TTTCTCATCT CAGAAAACAA GAAAGATGCA
1801 ATACAGTCTC TTGGGAAAAG CAAGCAACAG CCTCATTGCC ACAGAGGGGG
1851 AGACACAGAT TCCAAATTAT TAGAATAACT GGAAGCTTTC AAGTGTAAGA
1901 ATTGGTTTAA CAGCCTTTTT GACTGATATT ATTTAATTTT ACCAAGAAGG
1951 CTAAAATGCC CTCACAGATC AACTTAGGGG AATTATAATG AACTTCAGTT
2001 CAATTCAGAC TATACCTAAA AGGAAACTCA ATTTGCTAAC CATATATGTT
2051 AGCCATGACA AATTAAACAG TCACCATCGT CTACTATCAT TGTGACTGTT
2101 ACCACATCTT TCTCCCTGAG AAAAGCAGAG ATGGTTGTTC ACTATTCAGG
2151 ATAATACTGA AGTGGAAATC CTCCTGTCTG GCTATATCCA TTGCACTCCT
2201 TCCTTAATGA GATTGAGTTC CTGATTTTAA TGGGCTTGGC AATGAGGGCT
2251 TGAGGTTTCT GGCCCTGTCA AGGTCTTGTT GATGCCTGGT CCCAGGTGTG
2301 GTAGGTGATA TACAGCACTT GCTGATGGCA ATTGGGTTTG ATTCTATATT
2351 CAGCAAAGTG GATATATAAT CCTGACCTCT TTAGATAGAA AGAGAAAGAG
2401 AGGCAGAAGA AATATAGTAT TCTTCTGGCT ATCCTCAAGG CCCAGGGCAG
2451 AGAGTCTCAG AATGAAAATC TCAGCAAGTT CCAAGATTGG AATTTTGCAG
2501 GTTGATGATG CAAACAGCCC GGGGCAGAAA CTGGGACCTC CTTTCAGATT
2551 ATATCTCAAA GATTTTCAAG AGCCATCTGA GTGCTGCCGA GCTGCAAGAA
2601 AATAATACCA CACAAAATGT GAAACACATG GCCTCCCTGC TACCCTTCCA
2651 CCTCCCAGCT GAAGATTATA ATCTCCTGCC TTTCACTTTT TCTTAATGAT
```

FIGURE 3A

```
2701 TTTAACTGGT GAGCTGTTAA AAAGCTATTA GTATGGCTGG TGCCACTTGT
2751 CTATCCTGTA CTGCAAACAG AAGTGCACGC CGTAGTCAAT TAAGTGCTTG
2801 GAGAATAAAA AATTTTAAGG AGCACTAATA AAAAAATTCA TCAATTATGT
2851 GTGCTCCATT TAATACATGG TTGCTTAAAA TAAAATTTCC CAAACATATG
2901 TTCATTATGG ATTGCAGCAG GCTGGGAACC AGTGGCTTTA TTTATGCATT
2951 TAAAGTCTTG GTCTGACTGG GGAACCAGAA AAATGAAAAG TTAGTTGCAA
3001 TGAGCTTAAA GTGTCTCTGT CTTGCTTGCA GGCTACAACC CATTTGCCCC
3051 ATTGAAGGTC GACTGGGTGG AGCCCGCACT CAGGCTGAAT TCCCACTTCG
3101 CGCCCTGCAG TTTAAGCGTG GCCTGCTGCA CGAGTTCCGG AAGGGCAACG
3151 CTTCCAAGGA GCAGGTTCGC CTCCATGACC TGGTCCAGCA GCTCCCCAAG
3201 GCCATTATCA TTGGGGTGAG GAAAGGAGGC ACAAGGGCCC TGCTTGAAAT
3251 GCTGAACCTA CATCCGGCAG TAGTCAAAGC CTCTCAAGAA ATCCACTTTT
3301 TTGATAATGA TGAGAATTAT GGTAAGGGCA TTGAGTGGTA TAGGAAAAAG
3351 ATGCCTTTTT CCTACCCTCA GCAAATCACA ATTGAAAAGA GCCCAGCATA
3401 TTTTATCACA GAGGAGGTTC CAGAAAGGAT TTACAAAATG AACTCATCCA
3451 TCAAGTTGTT GATCATTGTC AGGGAGCCAA CCACAAGAGC TATTTCTGAT
3501 TATACTCAGG TGCTAGAGGG GAAGGAGAGG AAGAACAAAA CTTATTACAA
3551 GTTTGAGAAG CTGGCCATAG ACCCTAATAC ATGCGAAGTG AACACAAAAT
3601 ACAAAGCAGT AAGAACCAGC ATCTACACCA AACATCTGGA AAGGTGGTTG
3651 AAATACTTTC CAATTGAGCA ATTTCATGTC GTCGATGGAG ATCGCCTCAT
3701 CACGGAACCT CTGCCAGAAC TTCAGCTCGT GGAGAAGTTC CTAAATCTGC
3751 CTCCAAGGAT AAGTCAATAC AATTTATACT TCAATGCTAC CAGAGGGTTT
3801 TACTGCTTGC GGTTTAATAT TATCTTTAAT AAGTGCCTGG CGGGCAGCAA
3851 GGGGCGCATT CATCCAGAGG TGGACCCCTC TGTCATTACT AAATTGCGCA
3901 AATTCTTTCA TCCTTTTAAT CAAAAATTTT ACCAGATCAC TGGGAGGACA
3951 TTGAACTGGC CCTAAAATAA TATGTCATAC AACACTATGT GTTGTGCCTG
4001 GAGACACACA ATGTCTCCTG TAGATTAAAA TATGCACTTT TCCTAGGCAG
4051 AGCTATCCAA GTCATTTTTC CATGTATATT TGTACATACG CAGTGTGTGA
4101 CCAAATATAA GATCAGTTCT TTTTCTACTG AAAATTTACG AAAAAAAAAA
4151 AATTGCTGTC TGCATAGTCG CATCTTTTAA GCTATTTACA AAAGAGAAGA
4201 GGTGGTGGTA TTGGGGGAAA GTGACTTCAG CTATTCTCAA AGAGTTAGTC
4251 TTCCTTTGAT TCAGAATTTG TCACCCGCCA TTTTCATAGA TTTAAGCCAA
4301 AAGATAAATG TGTGAAAATG TACCAATGGC TGCGAAGCTT CAGGAAGTAG
4351 AGGATCCAGT GATGCATTTT TTTTTTCCTA AGGGAAAGCT GGCTCTTTAA
4401 TTCAGATGCT GAATTGGTGC CATGAAAACA GAAAATGCTA TTTTCTTATT
4451 ATTTAAAAGA ACGTCTTATC TCATAAAATT GACATTGTTC CAAAGTTCTT
4501 GTGGTGATTT TGCACTATTG TTTTCTCGTA TGGACCATGG TGTCACTTGT
4551 AGCATGTCAA TCACACATTG GAAAGTCAAG TCCTTTTACT TCCATGTTGT
4601 ATGTCAACAG AGAGAAATGT CATGTACATA ATGTATATTG TTGTAAATAC
4651 TGGTTTCACA CTAAGTAATT CTATTTTGTA AACTGAATAT GGCTATTTAA
4701 TTTATTGTGA AAATTAAATT TATTGTGGTA TTTAAAAATG GAATGGATTA
4751 AAATTACTCT ATGTGCAATT TTTTTTTTTT TTACTCATTT TGTTTTACGT
4801 GCCCCCTGCT GGCTTCCAAA ATGGAAGCTG TTTACGTGCA TATGAGAGCA
4851 CTTGGAAAGA TGTGCTTCCC TGCTGGATTT CTGTACCCCA GTGAAAATGT
4901 ATTTATGAAG TGAGGTTGAG TATATTAAAA AAGAAAAACC TCAACCATCT
4951 GGAAATCAAG TATAATAGCC ACCTCAAAGA ACCCTAGTGC TGCTCTGCTA
5001 CAACTTTGTA ACAATTAATT TACTCGCAGT TGCTGCTGCT CAGG (SEQ ID NO:3)
```

FEATURES:
Start:  3000
Exon:   3000-3962
Stop:   3963

FIGURE 3B

SNPs:

| DNA Position | Major | Minor | Domain | Protein Position | Major | Minor |
|---|---|---|---|---|---|---|
| 155 | C | G | Beyond ORF(5') | | | |
| 370 | A | T | Beyond ORF(5') | | | |
| 2775 | G | A | Beyond ORF(5') | | | |
| 4240 | A | G | Beyond ORF(3') | | | |

Context:

DNA Position

155
ATTAGCTTCCAATCATTTACCTTTTACTTAGTAATTGATCTAATGATCACTAATGCATTA
TTATTTAGTTGATGATTCTTTTCATTTTTTTAACTCTGTCTCTAGTCTCTAAGGGGATAG
CTTTTATTTGGAATTGAATTGTTTGGTGGGCTTT
[C,G]
TAAAAGCCTCTCACTTCAGACTTTGAGATTATGTCTGAAGGTAACAGGCTTATTTAGGCC
CACTCTCCAGTAACTGAAGACCCTGCTTTCTGGGAGGGAGACAGAGGTTACTTCTACCAT
CCCTTCCAATCCTAAACCTGTATGATTTTTCAGTCTGGGACCCATACTCAGAATCCATGC
TTTCAGAAGTGGGAAAGAATATGATATTTTCTCAAATTTTCACATTCTATCTTGAGTTAG
GGAGTCCAAAAAGCGACTATTCTGCAGGATGTGATCTCCCAGGGTAGAAGATAGAAAGAG

370
TGATGATTCTTTTCATTTTTTTAACTCTGTCTCTAGTCTCTAAGGGGATAGCTTTTATTT
GGAATTGAATTGTTTGGTGGGCTTTCTAAAAGCCTCTCACTTCAGACTTTGAGATTATGT
CTGAAGGTAACAGGCTTATTTAGGCCCACTCTCCAGTAACTGAAGACCCTGCTTTCTGGG
AGGGAGACAGAGGTTACTTCTACCATCCCTTCCAATCCTAAACCTGTATGATTTTTCAGT
CTGGGACCCATACTCAGAATCCATGCTTTCAGAAGTGGGAAAGAATATGATATTTTCTCA
[A,T]
ATTTTCACATTCTATCTTGAGTTAGGGAGTCCAAAAAGCGACTATTCTGCAGGATGTGAT
CTCCCAGGGTAGAAGATAGAAAGAGGAAGGAAGTAAAGAAGGAAAATGACCCTTTCTACA
AGTGGGGAAATTCCATTTGACCTCAAACAAAGCAGAGACTGTCTATATCAGCCACTCTCA
GCCAGGGTACTATGAAAGAATTAAATCCTACAAAAAAGAATTTGAGTGACTGTTTCCTCA
ATTCTTCCAAGGATGGTACTAGCATCATTCTAGGTGCTTAGGACAGAAATCCATCAATGG

2775
CAAGTTCCAAGATTGGAATTTTTGCAGGTTGATGATGCAAACAGCCCGGGGCAGAAACTGG
GACCTCCTTTCAGATTATATCTCAAAGATTTTCAAGAGCCATCTGAGTGCTGCCGAGCTG
CAAGAAAATAATACCACACAAAATGTGAAACACATGGCCTCCCTGCTACCCTTCCACCTC
CCAGCTGAAGATTATAATCTCCTGCCTTTCACTTTTTCTTAATGATTTTAACTGGTGAGC
TGTTAAAAAGCTATTAGTATGGCTGGTGCCACTTGTCTATCCTGTACTGCAAACAGAAGT
[G,A]
CACGCCGTAGTCAATTAAGTGCTTGGAGAATAAAAAATTTTAAGGAGCACTAATAAAAAA
ATTCATCAATTATGTGTGCTCCATTTAATACATGGTTGCTTAAAATAAAATTTCCCAAAC
ATATGTTCATTATGGATTGCAGCAGGCTGGGAACCAGTGGCTTTATTTATGCATTTAAAG
TCTTGGTCTGACTGGGGAACCAGAAAAATGAAAAGTTAGTTGCAATGAGCTTAAAGTGTC
TCTGTCTTGCTTGCAGGCTACAACCCATTTGCCCCATTGAAGGTCGACTGGGTGGAGCCC

4240
CTGGGAGGACATTGAACTGGCCCTAAAATAATATGTCATACAACACTATGTGTTGTGCCT
GGAGACACACAATGTCTCCTGTAGATTAAAATATGCACTTTTCCTAGGCAGAGCTATCCA
AGTCATTTTTTCCATGTATATTTGTACATACGCAGTGTGTGACCAAATATAAGATCAGTTC

FIGURE 3C

```
TTTTTCTACTGAAAATTTACGAAAAAAAAAAAAATTGCTGTCTGCATAGTCGCATCTTTTA
AGCTATTTACAAAAGAGAAGAGGTGGTGGTATTGGGGGAAAGTGACTTCAGCTATTCTCA
[A,G]
AGAGTTAGTCTTCCTTTGATTCAGAATTTGTCACCCGCCATTTTCATAGATTTAAGCCAA
AAGATAAATGTGTGAAAATGTACCAATGGCTGCGAAGCTTCAGGAAGTAGAGGATCCAGT
GATGCATTTTTTTTTTCCTAAGGGAAAGCTGGCTCTTTAATTCAGATGCTGAATTGGTGC
CATGAAAACAGAAAATGCTATTTTCTTATTATTTAAAAGAACGTCTTATCTCATAAAATT
GACATTGTTCCAAAGTTCTTGTGGTGATTTTGCACTATTGTTTTCTCGTATGGACCATGG
```

Chromosome map:
chromosome 6.

FIGURE 3D

SEQUENCE LISTING

<160> NUMBER OF SEQ ID NOS: 4

<210> SEQ ID NO 1
<211> LENGTH: 970
<212> TYPE: DNA
<213> ORGANISM: Homo sapien

<400> SEQUENCE: 1

```
atgagcttaa agtgtctctg tcttgcttgc aggctacaac ccatttgccc cattgaaggt      60
cgactgggtg gagcccgcac tcaggctgaa ttcccacttc gcgccctgca gtttaagcgt     120
ggcctgctgc acgagttccg gaagggcaac gcttccaagg agcaggttcg cctccatgac     180
ctggtccagc agctccccaa ggccattatc attggggtga ggaaaggagg cacaagggcc     240
ctgcttgaaa tgctgaacct acatccggca gtagtcaaag cctctcaaga aatccacttt     300
tttgataatg atgagaatta tggtaagggc attgagtggt ataggaaaaa gatgcctttt     360
tcctaccctc agcaaatcac aattgaaaag agcccagcat attttatcac agaggaggtt     420
ccagaaagga tttacaaaat gaactcatcc atcaagttgt tgatcattgt cagggagcca     480
accacaagag ctatttctga ttatactcag gtgctagagg ggaaggagag gaagaacaaa     540
acttattaca agtttgagaa gctggccata gaccctaata catgcgaagt gaacacaaaa     600
tacaaagcag taagaaccag catctacacc aaacatctgg aaaggtggtt gaaatacttt     660
ccaattgagc aatttcatgt cgtcgatgga gatcgcctca tcacggaacc tctgccagaa     720
cttcagctcg tggagaagtt cctaaatctg cctccaagga taagtcaata caatttatac     780
ttcaatgcta ccagagggtt ttactgcttg cggtttaata ttatctttaa taagtgcctg     840
gcgggcagca agggcgcat tcatccagag gtggacccct ctgtcattac taaattgcgc     900
aaattctttc atcctttaa tcaaaaattt taccagatca ctgggaggac attgaactgg     960
ccctaagggc                                                             970
```

<210> SEQ ID NO 2
<211> LENGTH: 321
<212> TYPE: PRT
<213> ORGANISM: Homo sapien

<400> SEQUENCE: 2

```
Met Ser Leu Lys Cys Leu Cys Leu Ala Cys Arg Leu Gln Pro Ile Cys
  1               5                  10                  15

Pro Ile Glu Gly Arg Leu Gly Gly Ala Arg Thr Gln Ala Glu Phe Pro
             20                  25                  30

Leu Arg Ala Leu Gln Phe Lys Arg Gly Leu Leu His Glu Phe Arg Lys
         35                  40                  45

Gly Asn Ala Ser Lys Glu Gln Val Arg Leu His Asp Leu Val Gln Gln
     50                  55                  60

Leu Pro Lys Ala Ile Ile Ile Gly Val Arg Lys Gly Gly Thr Arg Ala
 65                  70                  75                  80

Leu Leu Glu Met Leu Asn Leu His Pro Ala Val Val Lys Ala Ser Gln
                 85                  90                  95

Glu Ile His Phe Phe Asp Asn Asp Glu Asn Tyr Gly Lys Gly Ile Glu
            100                 105                 110

Trp Tyr Arg Lys Lys Met Pro Phe Ser Tyr Pro Gln Gln Ile Thr Ile
        115                 120                 125

Glu Lys Ser Pro Ala Tyr Phe Ile Thr Glu Glu Val Pro Glu Arg Ile
```

|     |     |     |     | 130 |     |     |     | 135 |     |     |     | 140 |     |     |
| --- | --- | --- | --- | --- | --- | --- | --- | --- | --- | --- | --- | --- | --- | --- |
| Tyr | Lys | Met | Asn | Ser | Ser | Ile | Lys | Leu | Leu | Ile | Ile | Val | Arg | Glu | Pro |
| 145 |     |     |     |     | 150 |     |     |     |     | 155 |     |     |     |     | 160 |
| Thr | Thr | Arg | Ala | Ile | Ser | Asp | Tyr | Thr | Gln | Val | Leu | Glu | Gly | Lys | Glu |
|     |     |     |     | 165 |     |     |     |     | 170 |     |     |     |     | 175 |     |
| Arg | Lys | Asn | Lys | Thr | Tyr | Tyr | Lys | Phe | Glu | Lys | Leu | Ala | Ile | Asp | Pro |
|     |     |     | 180 |     |     |     |     | 185 |     |     |     |     | 190 |     |     |
| Asn | Thr | Cys | Glu | Val | Asn | Thr | Lys | Tyr | Lys | Ala | Val | Arg | Thr | Ser | Ile |
|     |     |     | 195 |     |     |     |     | 200 |     |     |     |     | 205 |     |     |
| Tyr | Thr | Lys | His | Leu | Glu | Arg | Trp | Leu | Lys | Tyr | Phe | Pro | Ile | Glu | Gln |
|     | 210 |     |     |     |     | 215 |     |     |     |     | 220 |     |     |     |     |
| Phe | His | Val | Val | Asp | Gly | Asp | Arg | Leu | Ile | Thr | Glu | Pro | Leu | Pro | Glu |
| 225 |     |     |     |     | 230 |     |     |     |     | 235 |     |     |     |     | 240 |
| Leu | Gln | Leu | Val | Glu | Lys | Phe | Leu | Asn | Leu | Pro | Pro | Arg | Ile | Ser | Gln |
|     |     |     |     | 245 |     |     |     |     | 250 |     |     |     |     | 255 |     |
| Tyr | Asn | Leu | Tyr | Phe | Asn | Ala | Thr | Arg | Gly | Phe | Tyr | Cys | Leu | Arg | Phe |
|     |     |     | 260 |     |     |     |     | 265 |     |     |     |     | 270 |     |     |
| Asn | Ile | Ile | Phe | Asn | Lys | Cys | Leu | Ala | Gly | Ser | Lys | Gly | Arg | Ile | His |
|     |     |     | 275 |     |     |     |     | 280 |     |     |     |     | 285 |     |     |
| Pro | Glu | Val | Asp | Pro | Ser | Val | Ile | Thr | Lys | Leu | Arg | Lys | Phe | Phe | His |
|     | 290 |     |     |     |     | 295 |     |     |     |     | 300 |     |     |     |     |
| Pro | Phe | Asn | Gln | Lys | Phe | Tyr | Gln | Ile | Thr | Gly | Arg | Thr | Leu | Asn | Trp |
| 305 |     |     |     |     | 310 |     |     |     |     | 315 |     |     |     |     | 320 |
| Pro |     |     |     |     |     |     |     |     |     |     |     |     |     |     |     |

<210> SEQ ID NO 3
<211> LENGTH: 5044
<212> TYPE: DNA
<213> ORGANISM: Homo sapien

<400> SEQUENCE: 3

```
attagcttcc aatcatttac cttttactta gtaattgatc taatgatcac taatgcatta      60
ttatttagtt gatgattctt ttcattttt taactctgtc tctagtctct aaggggatag     120
cttttatttg gaattgaatt gtttggtggg ctttctaaaa gcctctcact tcagactttg     180
agattatgtc tgaaggtaac aggcttattt aggcccactc tccagtaact gaagaccctg     240
ctttctggga gggagacaga ggttacttct accatccctt ccaatcctaa acctgtatga     300
tttttcagtc tgggacccat actcagaatc catgctttca gaagtgggaa agaatatgat     360
attttctcaa attttcacat tctatcttga gttagggagt ccaaaaagcg actattctgc     420
aggatgtgat ctcccagggt agaagataga agaggaagg aagtaaagaa ggaaaatgac     480
cctttctaca agtggggaaa ttccatttga cctcaaacaa agcagagact gtctatatca     540
gccactctca gccagggtac tatgaaagaa ttaaatccta caaaaaagaa tttgagtgac     600
tgtttcctca attcttccaa ggatggtact agcatcattc taggtgctta ggacagaaat     660
ccatcaatgg atgccttatg gaattagagc ttaattctca accagaaccc aagaagaact     720
gaaagatgaa cttgtattat tccaatcagt gtcacaatta aaagcatctt tgcctatgta     780
tctattgata attttacatc ctccatttaa agccctagta cattaatctc attaacaaat     840
ttataaaaac aaaattcatg tttctctaaa ctattaaccg ggttaaatcc tgttttttaa     900
aagctgtcta ggccaggcac agtagctcac gcctgtaatc ccagcacttt gggaggctga     960
ggcaggcgaa tcacgagatc aggagttcaa gaccagccag gccaacatgg tgaaaccttg    1020
```

-continued

```
tctctactaa aaatacaaaa attagctggg tatggtggcg caggcctgta atcccagcta    1080
ctcgggaggc tgaggcagga gaatctcttg aacccaggag acagagattg cagtgagcca    1140
agatcgtgcc actgcactgc agcctaggca acagaccaag actccgtctc aaaaaaaaaa    1200
gaaaaaaaag ttgtctatat tttcacactt tccacaatga gcatgagttg ttttaaaaat    1260
cataaaaaag aaacatcgtg aaaagtagta tacattgata tttttcctta agcattatga    1320
tagatagctg tttaaacaga acaaagacca agaccatgct cctcaattct gcagaacagg    1380
ctgagtgtat tagtccgttt tcacagtgct ataaagacat acctgagact gagtaattta    1440
taaagaaaaa aggtttaatt gacacacagt tctgcatggc tggggaagcc tcagaaaact    1500
tacaatcatg gcagaaggca aagaagaagc aaggcacgtc ttacttggtg gcaggagaga    1560
gagggagctt gcaggggggcg gtgccacaca gttttaaacc atcaaatctc atgagaactc    1620
actatcatga aaacaagggg taaatacacc cccataatcc agtcacctcc caccaagccc    1680
ctcctccgac atgtggggat tacaattcgg gatgagattt gggtgggggc acagagccaa    1740
accatatcac tgggcatgac cttgaggttg tttctcatct cagaaaacaa gaaagatgca    1800
atacagtctc ttgggaaaag caagcaacag cctcattgcc acagagggg agacacagat     1860 tccaaattat tagaataact ggaagctttc aagtgtaaga attggtttaa cagccttttt    1920
gactgatatt atttaatttt accaagaagg ctaaatgcc ctcacagatc aacttagggg     1980
aattataatg aacttcagtt caattcagac tatacctaaa aggaaactca atttgctaac    2040
catatatgtt agccatgaca aattaaacag tcaccatcgt ctactatcat tgtgactgtt    2100
accacatctt tctccctgag aaaagcagag atggttgttc actattcagg ataatactga    2160
agtggaaatc ctcctgtctg gctatatcca ttgcactcct tccttaatga gattgagttc    2220 ctgatttaa tgggcttggc aatgagggct tgaggtttct ggccctgtca aggtcttgtt      2280
gatgcctggt cccaggtgtg gtaggtgata tacagcactt gctgatggca attgggtttg    2340
attctatatt cagcaaagtg gatatataat cctgacctct ttagatagaa agagaaagag    2400
aggcagaaga aatatagtat tcttctggct atcctcaagg cccagggcag agagtctcag    2460
aatgaaaatc tcagcaagtt ccaagattgg aattttgcag gttgatgatg caaacagccc    2520
ggggcagaaa ctgggacctc ctttcagatt atatctcaaa gattttcaag agccatctga    2580
gtgctgccga gctgcaagaa aataatacca cacaaaatgt gaaacacatg gcctccctgc    2640 taccccttcca cctcccagct gaagattata atctcctgcc tttcactttt tcttaatgat    2700
tttaactggt gagctgttaa aaagctatta gtatggctgg tgccacttgt ctatcctgta    2760
ctgcaaacag aagtgcacgc cgtagtcaat taagtgcttg gagaataaaa aattttaagg    2820
agcactaata aaaaaattca tcaattatgt gtgctccatt taatacatgg ttgcttaaaa    2880
taaaatttcc caaacatatg ttcattatgg attgcagcag gctgggaacc agtggcttta    2940
tttatgcatt taaagtcttg gtctgactgg ggaaccagaa aaatgaaaag ttagttgcaa    3000
tgagcttaaa gtgtctctgt cttgcttgca ggctacaacc catttgcccc attgaaggtc    3060
gactgggtgg agcccgcact caggctgaat tcccacttcg cgccctgcag tttaagcgtg    3120
gcctgctgca cgagttccgg aagggcaacg cttccaagga gcaggttcgc ctccatgacc    3180
tggtccagca gctcccccaag gccattatca ttggggtgag gaaggaggc acaagggccc    3240 tgcttgaaat gctgaaccta catccggcag tagtcaaagc ctctcaagaa atccacttttt   3300 ttgataatga tgagaattat ggtaagggca ttgagtggta taggaaaaag atgcctttttt   3360 cctaccctca gcaaatcaca attgaaaaga gcccagcata ttttatcaca gaggaggttc    3420
```

-continued

```
cagaaaggat ttacaaaatg aactcatcca tcaagttgtt gatcattgtc agggagccaa    3480
ccacaagagc tatttctgat tatactcagg tgctagaggg gaaggagagg aagaacaaaa    3540
cttattacaa gtttgagaag ctggccatag accctaatac atgcgaagtg aacacaaaat    3600
acaaagcagt aagaaccagc atctacacca aacatctgga aggtggttg aaatactttc     3660 caattgagca atttcatgtc gtcgatggag atcgcctcat cacggaacct ctgccagaac    3720
ttcagctcgt ggagaagttc ctaaatctgc ctccaaggat aagtcaatac aatttatact    3780
tcaatgctac cagagggttt tactgcttgc ggtttaatat tatctttaat aagtgcctgg    3840
cgggcagcaa ggggcgcatt catccagagg tggacccctc tgtcattact aaattgcgca    3900
aattctttca tccttttaat caaaaatttt accagatcac tgggaggaca ttgaactggc    3960
cctaaaataa tatgtcatac aacactatgt gttgtgcctg agacacaca atgtctcctg      4020 tagattaaaa tatgcacttt tcctaggcag agctatccaa gtcattttc catgtatatt      4080 tgtacatacg cagtgtgtga ccaaatataa gatcagttct ttttctactg aaaatttacg    4140
aaaaaaaaaa aattgctgtc tgcatagtcg catcttttaa gctatttaca aaagagaaga    4200
ggtggtggta ttgggggaaa gtgacttcag ctattctcaa agagttagtc ttcctttgat    4260
tcagaatttg tcacccgcca ttttcataga tttaagccaa aagataaatg tgtgaaaatg    4320
taccaatggc tgcgaagctt caggaagtag aggatccagt gatgcatttt ttttttccta    4380
agggaaagct ggctctttaa ttcagatgct gaattggtgc catgaaaaca gaaaatgcta    4440
ttttcttatt atttaaaaga acgtcttatc tcataaaatt gacattgttc caaagttctt    4500
gtggtgattt tgcactattg ttttctcgta tggaccatgg tgtcacttgt agcatgtcaa    4560
tcacacattg gaaagtcaag tccttttact tccatgttgt atgtcaacag agagaaatgt    4620
catgtacata atgtatattg ttgtaaatac tggtttcaca ctaagtaatt ctattttgta    4680
aactgaatat ggctatttaa tttattgtga aaattaaatt tattgtggta tttaaaaatg    4740
gaatggatta aaattactct atgtgcaatt ttttttttt ttactcattt tgttttacgt     4800 gcccctgct ggcttccaaa atggaagctg tttacgtgca tatgagagca cttggaaaga    4860
tgtgcttccc tgctggattt ctgtaccca gtgaaaatgt atttatgaag tgaggttgag    4920
tatattaaaa aagaaaaacc tcaaccatct ggaaatcaag tataatagcc acctcaaaga    4980
accctagtgc tgctctgcta caactttgta acaattaatt tactcgcagt tgctgctgct    5040
cagg                                                                5044
```

<210> SEQ ID NO 4
<211> LENGTH: 255
<212> TYPE: PRT
<213> ORGANISM: Homo sapien

<400> SEQUENCE: 4

```
Gln Gln Leu Pro Gln Thr Ile Ile Ile Gly Val Arg Lys Gly Gly Thr
 1               5                  10                  15

Arg Ala Leu Leu Glu Met Leu Ser Leu His Pro Asp Val Ala Ala Ala
                20                  25                  30

Glu Asn Glu Val His Phe Phe Asp Trp Glu Glu His Tyr Ser His Gly
            35                  40                  45

Leu Gly Trp Tyr Leu Ser Gln Met Pro Phe Ser Trp Pro His Gln Leu
        50                  55                  60

Thr Val Glu Lys Thr Pro Ala Tyr Phe Thr Ser Pro Lys Val Pro Glu
 65                  70                  75                  80
```

-continued

```
Arg Val Tyr Ser Met Asn Pro Ser Ile Arg Leu Leu Leu Ile Leu Arg
             85                  90                  95

Asp Pro Ser Glu Arg Val Leu Ser Asp Tyr Thr Gln Val Phe Tyr Asn
            100                 105                 110

His Met Gln Lys His Lys Pro Tyr Pro Ser Ile Glu Glu Phe Leu Val
            115                 120                 125

Arg Asp Gly Arg Leu Asn Val Asp Tyr Lys Ala Leu Asn Arg Ser Leu
    130                 135                 140

Tyr His Val His Met Gln Asn Trp Leu Arg Phe Phe Pro Leu Arg His
145                 150                 155                 160

Ile His Ile Val Asp Gly Asp Arg Leu Ile Arg Asp Pro Phe Pro Glu
            165                 170                 175

Ile Gln Lys Val Glu Arg Phe Leu Lys Leu Ser Pro Gln Ile Asn Ala
            180                 185                 190

Ser Asn Phe Tyr Phe Asn Lys Thr Lys Gly Phe Tyr Cys Leu Arg Asp
            195                 200                 205

Ser Gly Arg Asp Arg Cys Leu His Glu Ser Lys Gly Arg Ala His Pro
    210                 215                 220

Gln Val Asp Pro Lys Leu Leu Asn Lys Leu His Glu Tyr Phe His Glu
225                 230                 235                 240

Pro Asn Lys Lys Phe Phe Glu Leu Val Gly Arg Thr Phe Asp Trp
                245                 250                 255
```

US 6,730,505 B2

ISOLATED HUMAN DRUG-METABOLIZING PROTEINS, NUCLEIC ACID MOLECULES ENCODING HUMAN DRUG-METABOLIZING PROTEINS, AND USES THEREOF

RELATED APPLICATIONS

The present application is a divisional of U.S. application Ser. No. 09/735,935, filed on Dec. 14, 2000, and issued on Jul. 16, 2002 as U.S. Pat. No. 6,420,150, which claims priority to U.S. Provisional Application No. 60/252,895, filed on Nov. 27, 2000.

FIELD OF THE INVENTION

The present invention is in the field of drug-metabolizing proteins that are related to the sulfotransferase drug-metabolizing enzyme subfamily, recombinant DNA molecules and protein production. The present invention specifically provides novel drug-metabolizing peptides and proteins and nucleic acid molecules encoding such protein molecules, for use in the development of human therapeutics and human therapeutic development.

BACKGROUND OF THE INVENTION

Drug-Metabolizing Proteins

Induction of drug-metabolizing enzymes ("DMEs") is a common biological response to xenobiotics, the mechanisms and consequences of which are important in academic, industrial, and regulatory areas of pharmacology and toxicology.

For most drugs, drug-metabolizing enzymes determine how long and how much of a drug remains in the body. Thus, developers of drugs recognize the importance of characterizing a drug candidate's interaction with these enzymes. For example, polymorphisms of the drug-metabolizing enzyme CYP2D6, a member of the cytochrome p450 ("CYP") superfamily, yield phenotypes of slow or ultra-rapid metabolizers of a wide spectrum of drugs including antidepressants, antipsychotics, beta-blockers, and antiarrhythmics. Such abnormal rates of drug metabolism can lead to drug ineffectiveness or to systemic accumulation and toxicity.

For pharmaceutical scientists developing a candidate drug, it is important know as early as possible in the design phase which enzymes metabolize the drug candidate and the speed with which they do it. Historically, the enzymes on a drug's metabolic pathway were determined through metabolism studies in animals, but this approach has now been largely supplanted by the use of human tissues or cloned drug-metabolizing enzymes to provide insights into the specific role of individual forms of these enzymes. Using these tools, the qualitative and quantitative fate of a drug candidate can be predicted prior to its first administration to humans. As a consequence, the selection and optimization of desirable characteristics of metabolism are possible early in the development process, thus avoiding unanticipated toxicity problems and associated costs subsequent to the drug's clinical investigation. Moreover, the effect of one drug on another's disposition can be inferred.

Known drug-metabolizing enzymes include the cytochrome p450 ("CYP") superfamily, N-acetyl transferases ("NAT"), UDP-glucuronosyl transferases ("UGT"), methyl transferases, alcohol dehydrogenase ("ADH"), aldehyde dehydrogenase ("ALDH"), dihydropyrimidine dehydrogenase ("DPD"), NADPH:quinone oxidoreductase ("NQO" or "DT diaphorase"), catechol O-methyltransferase ("COMT"), glutathione S-transferase ("GST"), histamine methyltransferase ("HMT"), sulfotransferases ("ST"), thiopurine methyltransferase ("TPMT"), and epoxide hydroxylase. Drug-metabolizing enzymes are generally classified into two phases according to their metabolic function. Phase I enzymes catalyze modification of functional groups, and phase II enzymes catalyze conjugation with endogenous substituents. These classifications should not be construed as exclusive nor exhaustive, as other mechanisms of drug metabolism have been discovered. For example, the use of active transport mechanisms been characterized as part of the process of detoxification.

Phase I reactions include catabolic processes such as deamination of aminases, hydrolysis of esters and amides, conjugation reactions with, for example, glycine or sulfate, oxidation by the cytochrome p450 oxidation/reduction enzyme system and degradation in the fatty acid pathway. Hydrolysis reactions occur mainly in the liver and plasma by a variety of non-specific hydrolases and esterases. Both deaminases and amidases, also localized in the liver and serum, carry out a large part of the catabolic process. Reduction reactions occur mainly intracellularly in the endoplasmic reticulum.

Phase II enzymes detoxify toxic substances by catalyzing their conjugation with water-soluble substances, thus increasing toxins' solubility in water and increasing their rate of excretion. Additionally, conjugation reduces the toxins' biological reactivity. Examples of phase II enzymes include glutathione S-transferases and UDP-glucuronosyl transferases, which catalyze conjugation to glutathione and glucuronic acid, respectively. Transferases perform conjugation reactions mainly in the kidneys and liver.

The liver is the primary site of elimination of most drugs, including psychoactive drugs, and contains a plurality of both phase I and phase II enzymes that oxidize or conjugate drugs, respectively.

Physicians currently prescribe drugs and their dosages based on a population average and fail to take genetic variability into account. The variability between individuals in drug metabolism is usually due to both genetic and environmental factors, in particular, how the drug-metabolizing enzymes are controlled. With certain enzymes, the genetic component predominates and variability is associated with variants of the normal, wild-type enzyme.

Most drug-metabolizing enzymes exhibit clinically relevant genetic polymorphisms. Essentially all of the major human enzymes responsible for modification of functional groups or conjugation with endogenous subsituents exhibit common polymorphisms at the genomic level. For example, polymorphisms expressing a non-functioning variant enzyme results in a sub-group of patients in the population who are more prone to the concentration-dependent effects of a drug. This sub-group of patients may show toxic side effects to a dose of drug that is otherwise without side effects in the general population. Recent development in genotyping allows identification of affected individuals. As a result, their atypical metabolism and likely response to a drug metabolized by the affected enzyme can be understood and predicted, thus permitting the physician to adjust the dose of drug they receive to achieve improved therapy.

A similar approach is also becoming important in identifying risk factors associated with the development of various cancers. This is because the enzymes involved in drug metabolism are also responsible for the activation and detoxification of chemical carcinogens. Specifically, the development of neoplasia is regulated by a balance between phase I enzymes, which activate carcinogens, and phase II enzymes, which detoxify them. Accordingly, an individual's susceptibility to cancer often involves the balance between these two processes, which is, in part, genetically determined and can be screened by suitable genotyping tests. Higher induction of phase I enzymes compared to phase II enzymes results in the generation of large amounts of electrophiles and reactive oxygen species and may cause DNA and membrane damage and other adverse effects leading to neoplasia. Conversely, higher levels of phase II enzyme expression can protect cells from various chemical compounds.

Abnormal activity of drug-metabolizing enzymes has been implicated in a range of human diseases, including cancer, Parkinson's disease, myetonic dystrophy, and developmental defects.

Cytochrome p450

An example of a phase I drug-metabolizing enzyme is the cytochrome p450 ("CYP") superfamily, the members of which comprise the major drug-metabolizing enzymes expressed in the liver. The CYP superfamily comprises heme proteins which catalyze the oxidation and dehydrogenation of a number of endogenous and exogenous lipophilic compounds. The CYP superfamily has immense diversity in its functions, with hundreds of isoforms in many species catalyzing many types of chemical reactions. The CYP superfamily comprises at least 30 related enzymes, which are divided into different families according to their amino acid homology. Examples of CYP families include CYP families 1, 2, 3 and 4, which comprise endoplasmic reticulum proteins responsible for the metabolism of drugs and other xenobiotics. Approximately 10–15 individual gene products within these four families metabolize thousands of structurally diverse compounds. It is estimated that collectively the enzymes in the CYP superfamily participate in the metabolism of greater than 80% of all available drugs used in humans. For example, the CYP 1A subfamily comprises CYP 1A2, which metabolizes several widely used drugs, including acetaminophen, amitriptyline, caffeine, clozapine, haloperidol, imipramine, olanzapine, ondansetron, phenacetin, propafenone, propranolol, tacrine, theophylline, verapamil. In addition, CYP enzymes play additional roles in the metabolism of some endogenous substrates including prostaglandins and steroids.

Some CYP enzymes exist in a polymorphic form, meaning that a small percentage of the population possesses mutant genes that alter the activity of the enzyme, usually by diminishing or abolishing activity. For example, a genetic polymorphism has been well characterized with the CYP 2C19 and CYP 2D6 genes. Substrates of CYP 2C19 include clomipramine, diazepam, imipramine, mephenytoin, moclobemide, omeprazole, phenytoin, propranolol, and tolbutamide. Substrates of CYP 2D6 include alprenolol, amitriptyline, chlorpheniramine, clomipramine, codeine, desipramine, dextromethorphan, encainide, fluoxetine, haloperidol, imipramine, indoramin, metoprolol, nortriptyline, ondansetron, oxycodone, paroxetine, propranolol, and propafenone. Polymorphic variants of these genes metabolize these substrates at different rates, which can effect a patient's effective therapeutic dosage.

While the substrate specificity of CYPs must be very broad to accommodate the metabolism of all of these compounds, each individual CYP gene product has a narrower substrate specificity defined by its binding and catalytic sites. Drug metabolism can thereby be regulated by changes in the amount or activity of specific CYP gene products. Methods of CYP regulation include genetic differences in the expression of CYP gene products (i.e., genetic polymorphisms), inhibition of CYP metabolism by other xenobiotics that also bind to the CYP, and induction of certain CYPs by the drug itself or other xenobiotics. Inhibition and induction of CYPs is one of the most common mechanisms of adverse drug interactions. For example, the CYP3A subfamily is involved in clinically significant drug interactions involving nonsedating antihistamines and cisapride that may result in cardiac dysrhythmias. In another example, CYP3A4 and CYP1A2 enzymes are involved in drug interactions involving theophylline. In yet another example, CYP2D6 is responsible for the metabolism of many psychotherapeutic agents. Additionallly, CYP enzymes metabolize the protease inhibitors used to treat patients infected with the human immunodeficiency virus. By understanding the unique functions and characteristics of these enzymes, physicians may better anticipate and manage drug interactions and may predict or explain an individual's response to a particular therapeutic regimen.

Examples of reactions catalyzed by the CYP superfamily include peroxidative reactions utilizing peroxides as oxygen donors in hydroxylation reactions, as substrates for reductive beta-scission, and as peroxyhemiacetal intermediates in the cleavage of aldehydes to formate and alkenes. Lipid hydroperoxides undergo reductive beta-cleavage to give hydrocarbons and aldehydic acids. One of these products, trans-4-hydroxynonenal, inactivates CYP, particularly alcohol-inducible 2E1, in what may be a negative regulatory process. Although a CYP iron-oxene species is believed to be the oxygen donor in most hydroxylation reactions, an iron-peroxy species is apparently involved in the deformylation of many aldehydes with desaturation of the remaining structure, as in aromatization reactions.

Examples of drugs with oxidative metabolism associated with CYP enzymes include acetaminophen, alfentanil, alprazolam, alprenolol, amiodarone, amitriptyline, astemizole, buspirone caffeine, carbamazepine, chlorpheniramine, cisapride, clomipramine, clomipramine, clozapine, codeine, colchicine, cortisol, cyclophosphamide, cyclosporine, dapsone, desipramine, dextromethorphan, diazepam, diclofenac, diltiazem, encainide, erythromycin, estradiol, felodipine, fluoxetine, fluvastatin, haloperidol, ibuprofen, imipramine, indinavir, indomethacin, indoramin, irbesartan, lidocaine, losartan, macrolide antibiotics, mephenytoin, methadone, metoprolol, mexilitene, midazolam, moclobemide, naproxen, nefazodone, nicardipine, nifedipine, nitrendipine, nortriptyline, olanzapine, omeprazole, ondansetron, oxycodone, paclitaxel, paroxetine, phenacetin, phenytoin, piroxicam, progesterone, propafenone, propranolol, quinidine, ritonavir, saquinavir, sertraline, sildenafil, S-warfarin, tacrine, tamoxifen, tenoxicam, terfenadine, testosterone, theophylline, timolol, tolbutamide, triazolam, verapamil, and vinblastine.

Abnormal activity of phase I enzymes has been implicated in a range of human diseases. For example, enhanced CYP2D6 activity has been related to malignancies of the bladder, liver, pharynx, stomach and lungs, whereas decreased CYP2D activity has been linked to an increased risk of Parkinson's disease. Other syndromes and developmental defects associated with deficiencies in the CYP superfamily include cerebrotendinous xanthomatosis, adrenal hyperplasia, gynecomastia, and myetonic dystrophy.

The CYP superfamily a major target for drug action and development. Accordingly, it is valuable to the field of pharmaceutical development to identify and characterize previously unknown members of the CYP superfamily.

UDP-Glucuronosyltransferases

Potential drug interactions involving phase II metabolism are increasingly being recognized. An important group of phase II enzymes involved in drug metabolism are the glucuronosyltransferases, especially the UDP-glucuronyltransferase ("UGT") superfamily. Members of the UGT superfamily catalyze the enzymatic addition of UDP glucuronic acid as a sugar donor to fat-soluble chemicals, a process which increases their solubility in water and increases their rate of excretion. In mammals, glucuronic acid is the main sugar that is used to prevent the accumulation of waste products of metabolism and fat-soluble chemicals from the environment to toxic levels in the body. Both inducers and inhibitors of glucuronosyltransferases are known and have the potential to affect the plasma concentration and actions of important drugs, including psychotropic drugs.

The UGT superfamily comprises several families of enzymes in several species defined with a nomenclature similar to that used to define members of the CYP superfamily. In animals, yeast, plants and bacteria there are at least 110 distinct known members of the UGT superfamily. As many as 33 families have been defined, with three families identified in humans. Different UGT families are defined as having <45% amino acid sequence homology; within subfamilies there is approximately 60% homology. The members of the UGT superfamily are part of a further superfamily of UDP glycosyltransferases found in animals, plants and bacteria.

The role of phase II enzymes, and of UGT enzymes in particular, is being increasingly recognized as important in psychopharmacology. UGT enzymes conjugate many important psychotropic drugs and are an important source of variability in drug response and drug interactions. For example, the benzodiazepines lorazepam, oxazepam, and temazepam undergo phase II reactions exclusively before being excreted into the urine.

Phase II enzymes metabolize and detoxify hazardous substances, such as carcinogens. The expression of genes encoding phase II enzymes is known to be up-regulated by hundreds of agents. For example, oltipraz is known to up-regulate phase II enzyme expression. Studies have demonstrated protection from the cancer-causing effects of carcinogens when selected phase II enzyme inducers are administered prior to the carcinogens. The potential use of phase II enzyme inducers in humans for prevention of cancers related to exposure to carcinogens has prompted studies aimed at understanding their molecular effects. Current biochemical and molecular biological research methodologies can be used to identify and characterize selective phase II enzyme inducers and their targets. Identification of genes responding to cancer chemopreventive agents will facilitate studies of their basic mechanism and provide insights about the relationship between gene regulation, enzyme polymorphism, and carcinogen detoxification.

Examples of drugs with conjugative metabolism associated with UGT enzymes include amitriptyline, buprenorphine, chlorpromazine, clozapine, codeine, cyproheptadine, dihydrocodeine, doxepin, imipramine, lamotrigine, lorazepam, morphine, nalorphine, naltrexone, temazepam, and valproate.

Abnormal activity of phase II enzymes has been implicated in a range of human diseases. For example, Gilbert syndrome is an autosomal dominant disorder caused by mutation in the UGT1 gene, and mutations in the UGT1A1 enzyme have been demonstrated to be responsible for Crigler-Najjar syndrome.

The UGT superfamily a major target for drug action and development. Accordingly, it is valuable to the field of pharmaceutical development to identify and characterize previously unknown members of the UGT superfamily.

Sulfotransferase

The sulfotransferases that act upon different substrates exhibit extensive structural diversity; indeed, similarity is greatest between members of this enzyme class that sulfate related substrates. The sulfotransferase includes the N-acetylglucosamine/glucuronic acid copolymerase, the N-deacetylase/N-sulfotransferase (NST), the glucuronic acid/iduronic acid epimerase, the iduronic acid/glucuronic acid 2-O-sulfotransferase, the glucosamine 6-O-sulfotransferase, and the glucosamine 3-O-sulfotransferase (3-OST). 3-OST and all known NST species possess a homologous carboxyl-terminal domain of ~260 residues that also exhibits homology to all known sulfotransferases. Given that this region constitutes >88% of the protein A-tagged r3-OST and so should contain the machinery for sulfation, that a common domain structure is shared by heparan sulfate sulfotransferases or at least by heparan glucosaminyl sulfotransferases. The cellular rate of anticoagulant heparan sulfate proteoglycan generation is determined by the level of the microsomal activity 'HS-act conversion activity', which is predominantly composed of the enzyme heparan sulfate D-glucosaminyl 3-O-sulfotransferase (3OST). Shworak et al., (*J Biol Chem* Oct. 31, 1997; 272(44):28008–19) cloned mouse and human 3OST cDNAs. The predicted 307-amino acid human 3OST protein shares 93% sequence similarity with mouse 3OST. The 3OST protein contains a signal sequence and 5 potential N-glycosylation sites. Both human and mouse 3OST have a calculated molecular mass of approximately 36 kD. The discrepancy between the observed and calculated molecular masses is due to glycosylation. The human and mouse 3OST proteins exhibited HS-act conversion and 3OST activities when expressed in vitro. Based on the site of heparan biosynthesis and on structural analysis of the 3OST protein, it is suggested that 3OST is an intraluminal Golgi enzyme. The Northern blot analysis of human cells showed that 3OST is expressed as a 1.7-kb mRNA.

Drug-metabolizing enzymes, particularly members of the sulfotransferase drug-metabolizing enzyme subfamily, are a major target for drug action and development. Accordingly, it is valuable to the field of pharmaceutical development to identify and characterize previously unknown members of this subfamily of drug-metabolizing proteins. The present invention advances the state of the art by providing a previously unidentified human drug-metabolizing proteins that have homology to members of the sulfotransferase drug-metabolizing enzyme subfamily.

SUMMARY OF THE INVENTION

The present invention is based in part on the identification of amino acid sequences of human drug-metabolizing enzyme peptides and proteins that are related to the sulfotransferase drug-metabolizing enzyme subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate drug-metabolizing enzyme activity in cells and tissues that express the drug-metabolizing enzyme. Experimental data as provided in FIG. 1 indicates expression in the lung.

DESCRIPTION OF THE FIGURE SHEETS

FIG. 1 provides the nucleotide sequence of a cDNA molecule or transcript sequence that encodes the drug-metabolizing enzyme protein of the present invention. (SEQ ID NO: 1) In addition, structure and functional information is provided, such as ATG start, stop and tissue distribution, where available, that allows one to readily determine specific uses of inventions based on this molecular sequence. Experimental data as provided in FIG. 1 indicates expression in the lung.

FIG. 2 provides the predicted amino acid sequence of the drug-metabolizing enzyme of the present invention. (SEQ ID NO: 2) In addition structure and functional information such as protein family, function, and modification sites is provided where available, allowing one to readily determine specific uses of inventions based on this molecular sequence.

FIG. 3 provides genomic sequences that span the gene encoding the drug-metabolizing enzyme protein of the present invention. (SEQ ID NO: 3) In addition structure and functional information, such as intron/exon structure, promoter location, etc., is provided where available, allowing one to readily determine specific uses of inventions based on this molecular sequence. 4 SNPs have been identified in the gene encoding the sulfotransferase protein provided by the present invention and are given in FIG. 3.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a drug-metabolizing enzyme protein or part of a drug-metabolizing enzyme protein and are related to the sulfotransferase drug-metabolizing enzyme subfamily. Utilizing these sequences, additional genomic sequences were assembled and transcript and/or cDNA sequences were isolated and characterized. Based on this analysis, the present invention provides amino acid sequences of human drug-metabolizing enzyme peptides and proteins that are related to the sulfotransferase drug-metabolizing enzyme subfamily, nucleic acid sequences in the form of transcript sequences, cDNA sequences and/or genomic sequences that encode these drug-metabolizing enzyme peptides and proteins, nucleic acid variation (allelic information), tissue distribution of expression, and information about the closest art known protein/peptide/domain that has structural or sequence homology to the drug-metabolizing enzyme of the present invention.

In addition to being previously unknown, the peptides that are provided in the present invention are selected based on their ability to be used for the development of commercially important products and services. Specifically, the present peptides are selected based on homology and/or structural relatedness to known drug-metabolizing enzyme proteins of the sulfotransferase drug-metabolizing enzyme subfamily and the expression pattern observed. Experimental data as provided in FIG. 1 indicates expression in the lung. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known sulfotransferase family or subfamily of drug-metabolizing enzyme proteins.

Specific Embodiments

Peptide Molecules

The present invention provides nucleic acid sequences that encode protein molecules that have been identified as being members of the drug-metabolizing enzyme family of proteins and are related to the sulfotransferase drug-metabolizing enzyme subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the drug-metabolizing enzyme peptides of the present invention, drug-metabolizing enzyme peptides, or peptides/proteins of the present invention.

The present invention provides isolated peptide and protein molecules that consist of, consist essentially of, or comprise the amino acid sequences of the drug-metabolizing enzyme peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the drug-metabolizing enzyme peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated drug-metabolizing enzyme peptide can be purified from cells that naturally express it, purified from cells that have been altered to express it (recombinant), or synthesized using known protein synthesis methods. Experimental data as provided in FIG. 1 indicates expression in the lung. For example, a nucleic acid molecule encoding the drug-metabolizing enzyme peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO: 2), for example, proteins encoded by the transcript/cDNA nucleic acid sequences shown in FIG. 1 (SEQ ID NO: 1) and the genomic sequences provided in FIG. 3 (SEQ ID NO: 3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO: 2), for example, proteins encoded by the transcript/cDNA nucleic acid sequences shown in FIG. 1 (SEQ ID NO: 1) and the genomic sequences provided in FIG. 3 (SEQ ID NO: 3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO: 2), for example, proteins encoded by the transcript/cDNA nucleic acid sequences shown in FIG. 1 (SEQ ID NO: 1) and the genomic sequences provided in FIG. 3 (SEQ ID NO: 3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the drug-metabolizing enzyme peptides of the present invention are the naturally occurring mature proteins. A brief description of how various types of these proteins can be made/isolated is provided below.

The drug-metabolizing enzyme peptides of the present invention can be attached to heterologous sequences to form chimeric or fusion proteins. Such chimeric and fusion proteins comprise a drug-metabolizing enzyme peptide operatively linked to a heterologous protein having an amino acid sequence not substantially homologous to the drug-metabolizing enzyme peptide. "Operatively linked" indicates that the drug-metabolizing enzyme peptide and the heterologous protein are fused in-frame. The heterologous protein can be fused to the N-terminus or C-terminus of the drug-metabolizing enzyme peptide.

In some uses, the fusion protein does not affect the activity of the drug-metabolizing enzyme peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant drug-metabolizing enzyme peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A drug-metabolizing enzyme peptide-encoding nucleic acid can be cloned into such an expression vector such that the fusion moiety is linked in-frame to the drug-metabolizing enzyme peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the drug-metabolizing enzyme peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part* 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(J):387 (1984)) (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the drug-metabolizing enzyme peptides of the present invention as well as being encoded by the same genetic locus as the drug-metabolizing enzyme peptide provided herein. As indicated by the data presented in FIG. 3, the map position was determined to be on chromosome 6 by ePCR.

Allelic variants of a drug-metabolizing enzyme peptide can readily be identified as being a human protein having a high degree (significant) of sequence homology/identity to at least a portion of the drug-metabolizing enzyme peptide as well as being encoded by the same genetic locus as the drug-metabolizing enzyme peptide provided herein. Genetic locus can readily be determined based on the genomic information provided in FIG. 3, such as the genomic sequence mapped to the reference human. As indicated by the data presented in FIG. 3, the map position was determined to be on chromosome 6 by ePCR. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a drug-metabolizing enzyme peptide encoding nucleic acid molecule under stringent conditions as more fully described below.

FIG. 3 provides information on SNPs that have been identified in a gene encoding the that drug-metabolizing enzyme proteins of the present invention. 4 SNP variants were found, of which all of them beyond ORFs.

Paralogs of a drug-metabolizing enzyme peptide can readily be identified as having some degree of significant sequence homology/identity to at least a portion of the drug-metabolizing enzyme peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a drug-metabolizing enzyme peptide encoding nucleic acid molecule under moderate to stringent conditions as more fully described below.

Orthologs of a drug-metabolizing enzyme peptide can readily be identified as having some degree of significant sequence homology/identity to at least a portion of the drug-metabolizing enzyme peptide as well as being encoded by a gene from another organism. Preferred orthologs will be isolated from mammals, preferably primates, for the development of human therapeutic targets and agents. Such orthologs will be encoded by a nucleic acid sequence that will hybridize to a drug-metabolizing enzyme peptide encoding nucleic acid molecule under moderate to stringent conditions, as more fully described below, depending on the degree of relatedness of the two organisms yielding the proteins.

Non-naturally occurring variants of the drug-metabolizing enzyme peptides of the present invention can readily be generated using recombinant techniques. Such variants include, but are not limited to deletions, additions and substitutions in the amino acid sequence of the drug-metabolizing enzyme peptide. For example, one class of substitutions are conserved amino acid substitution. Such substitutions are those that substitute a given amino acid in a drug-metabolizing enzyme peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant drug-metabolizing enzyme peptides can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as drug-metabolizing enzyme activity or in assays such as an in vitro proliferative activity. Sites that are critical for binding partner/substrate binding can also be determined by structural analysis such as crystallization, nuclear magnetic resonance or photoaffinity labeling (Smith et al., *J Mol. Biol.* 224:899–904 (1992); de Vos et al. *Science* 255:306–312 (1992)).

The present invention further provides fragments of the drug-metabolizing enzyme peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a drug-metabolizing enzyme peptide. Such fragments can be chosen based on the ability to retain one or more of the biological activities of the drug-metabolizing enzyme peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the drug-metabolizing enzyme peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in drug-metabolizing enzyme peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd Ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (*Meth. Enzymol.* 182: 626–646 (1990)) and Rattan et al (*Ann. N.Y. Acad. Sci.* 663:48–62 (1992)).

Accordingly, the drug-metabolizing enzyme peptides of the present invention also encompass derivatives or analogs in which a substituted amino acid residue is not one encoded by the genetic code, in which a substituent group is included, in which the mature drug-metabolizing enzyme peptide is fused with another compound, such as a compound to increase the half-life of the drug-metabolizing enzyme peptide (for example, polyethylene glycol), or in which the additional amino acids are fused to the mature drug-metabolizing enzyme peptide, such as a leader or secretory sequence or a sequence for purification of the mature drug-metabolizing enzyme peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a drug-metabolizing enzyme-effector protein interaction or drug-metabolizing enzyme-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

Substantial chemical and structural homology exists between the sulfotransferase protein described herein and heparan sulfotransferase (3-OST) (see FIG. 1). As discussed in the background, sulfotransferase are known in the art to be involved in drug metabolism and heparan biosynthesis. Accordingly, the sulfotransferase protein, and the encoding gene, provided by the present invention is useful for treating, preventing, and/or diagnosing disorders such as blood coagulation and disorders associated with drug metabolism.

The potential uses of the peptides of the present invention are based primarily on the source of the protein as well as the class/action of the protein. For example, drug-metabolizing enzymes isolated from humans and their human/mammalian orthologs serve as targets for identifying agents for use in mammalian therapeutic applications, e.g. a human drug, particularly in modulating a biological or pathological response in a cell or tissue that expresses the drug-metabolizing enzyme. Experimental data as provided in FIG. 1 indicates that drug-metabolizing enzyme proteins of the present invention are expressed in the lung. Specifically, a virtual northern blot shows expression in carcinoid lung. In addition, PCR-based tissue screening panel indicates expression in human and human fetal brain, human bone marrow, human colon, human fetal heart, human fetal liver, human fetal lung, human pancreas, human placenta. A large percentage of pharmaceutical agents are being developed that modulate the activity of drug-metabolizing enzyme proteins, particularly members of the sulfotransferase subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in the lung. Such uses can readily be determined using the information provided herein, that which is known in the art, and routine experimentation.

The drug-metabolizing enzyme polypeptides (including variants and fragments that may have been disclosed prior to the present invention) are useful for biological assays related to drug-metabolizing enzymes that are related to members of the sulfotransferase subfamily. Such assays involve any of the known drug-metabolizing enzyme functions or activities or properties useful for diagnosis and treatment of drug-metabolizing enzyme-related conditions that are specific for the subfamily of drug-metabolizing enzymes that the one of the present invention belongs to, particularly in cells and tissues that express the drug-metabolizing enzyme. Experimental data as provided in FIG. 1 indicates that drug-metabolizing enzyme proteins of the present invention are expressed in the lung. Specifically, a virtual northern blot shows expression in carcinoid lung. In addition, PCR-based tissue screening panel indicates expression in human and human fetal brain, human bone marrow, human colon, human fetal heart, human fetal liver, human fetal lung, human pancreas, human placenta.

The drug-metabolizing enzyme polypeptides are also useful in drug screening assays, in cell-based or cell-free systems. Cell-based systems can be native, i.e., cells that normally express the drug-metabolizing enzyme, as a biopsy or expanded in cell culture. Experimental data as provided in FIG. 1 indicates expression in the lung. In an alternate embodiment, cell-based assays involve recombinant host cells expressing the drug-metabolizing enzyme protein.

The polypeptides can be used to identify compounds that modulate drug-metabolizing enzyme activity of the protein in its natural state or an altered form that causes a specific disease or pathology associated with the drug-metabolizing enzyme. Both the drug-metabolizing enzymes of the present invention and appropriate variants and fragments can be used in high-throughput screens to assay candidate compounds for the ability to bind to the drug-metabolizing enzyme. These compounds can be further screened against a functional drug-metabolizing enzyme to determine the effect of the compound on the drug-metabolizing enzyme activity. Further, these compounds can be tested in animal or invertebrate systems to determine activity/effectiveness. Compounds can be identified that activate (agonist) or inactivate (antagonist) the drug-metabolizing enzyme to a desired degree.

Further, the drug-metabolizing enzyme polypeptides can be used to screen a compound for the ability to stimulate or inhibit interaction between the drug-metabolizing enzyme protein and a molecule that normally interacts with the drug-metabolizing enzyme protein. Such assays typically include the steps of combining the drug-metabolizing enzyme protein with a candidate compound under conditions that allow the drug-metabolizing enzyme protein, or fragment, to interact with the target molecule, and to detect the formation of a complex between the protein and the target or to detect the biochemical consequence of the interaction with the drug-metabolizing enzyme protein and the target.

Candidate compounds include, for example, 1) peptides such as soluble peptides, including Ig-tailed fusion peptides and members of random peptide libraries (see, e.g., Lam et al., Nature 354:82–84 (1991); Houghten et al., Nature 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al, Cell 72:767–778 (1993)); 3) antibodies (e.g., polyclonal, monoclonal, humanized, anti-idiotypic, chimeric, and single chain antibodies as well as Fab, $F(ab')_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant drug-metabolizing enzymes or appropriate fragments containing mutations that affect drug-metabolizing enzyme function and thus compete for substrate. Accordingly, a fragment that competes for substrate, for example with a higher affinity, or a fragment that binds substrate but does not allow release, is encompassed by the invention.

Any of the biological or biochemical functions mediated by the drug-metabolizing enzyme can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the drug-metabolizing enzyme can be assayed. Experimental data as provided in FIG. 1 indicates that drug-metabolizing enzyme proteins of the present invention are expressed in the lung. Specifically, a virtual northern blot shows expression in carcinoid lung. In addition, PCR-based tissue screening panel indicates expression in human and human fetal brain, human bone marrow, human colon, human fetal heart, human fetal liver, human fetal lung, human pancreas, human placenta.

Binding and/or activating compounds can also be screened by using chimeric drug-metabolizing enzyme proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native drug-metabolizing enzyme. Accordingly, a different set of signal transduction components is available as an end-point assay for activation. This allows for assays to be performed in other than the specific host cell from which the drug-metabolizing enzyme is derived.

The drug-metabolizing enzyme polypeptides are also useful in competition binding assays in methods designed to discover compounds that interact with the drug-metabolizing enzyme (e.g. binding partners and/or ligands). Thus, a compound is exposed to a drug-metabolizing enzyme polypeptide under conditions that allow the compound to bind or to otherwise interact with the polypeptide. Soluble drug-metabolizing enzyme polypeptide is also added to the mixture. If the test compound interacts with the soluble drug-metabolizing enzyme polypeptide, it decreases the amount of complex formed or activity from the drug-metabolizing enzyme target. This type of assay is particularly useful in cases in which compounds are sought that interact with specific regions of the drug-metabolizing enzyme. Thus, the soluble polypeptide that competes with the target drug-metabolizing enzyme region is designed to contain peptide sequences corresponding to the region of interest.

To perform cell free drug screening assays, it is sometimes desirable to immobilize either the drug-metabolizing enzyme protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of drug-metabolizing enzyme-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a drug-metabolizing enzyme-binding protein and a candidate compound are incubated in the drug-metabolizing enzyme protein-presenting wells and the amount of complex trapped in the well can be quantitated. Methods for detecting such complexes, in addition to those described above for the GST-immobilized complexes, include immunodetection of complexes using antibodies reactive with the drug-metabolizing enzyme protein target molecule, or which are reactive with drug-metabolizing enzyme protein and compete with the target molecule, as well as enzyme-linked assays which rely on detecting an enzymatic activity associated with the target molecule.

Agents that modulate one of the drug-metabolizing enzymes of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of drug-metabolizing enzyme protein activity identified according to these drug screening assays can be used to treat a subject with a disorder mediated by the drug-metabolizing enzyme pathway, by treating cells or tissues that express the drug-metabolizing enzyme. Experimental data as provided in FIG. 1 indicates expression in the lung. These methods of treatment include the steps of administering a modulator of drug-metabolizing enzyme activity in a pharmaceutical composition to a subject in need of such treatment, the modulator being identified as described herein.

In yet another aspect of the invention, the drug-metabolizing enzyme proteins can be used as "bait proteins" in a two-hybrid assay or three-hybrid assay (see, e.g., U.S. Pat. No. 5,283,317; Zervos et al. (1993) Cell 72:223–232; Madura et al. (1993) J. Biol. Chem. 268:12046–12054; Bartel et al. (1993) Biotechniques 14:920–924; Iwabuchi et al. (1993) Oncogene 8:1693–1696; and Brent WO94/10300), to identify other proteins, which bind to or interact with the drug-metabolizing enzyme and are involved in drug-metabolizing enzyme activity. Such drug-metabolizing enzyme-binding proteins are likely to be drug-metabolizing enzyme inhibitors.

The two-hybrid system is based on the modular nature of most transcription factors, which consist of separable DNA-binding and activation domains. Briefly, the assay utilizes two different DNA constructs. In one construct, the gene that codes for a drug-metabolizing enzyme protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a drug-metabolizing enzyme-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the drug-metabolizing enzyme protein.

This invention further pertains to novel agents identified by the above-described screening assays. Accordingly, it is within the scope of this invention to further use an agent identified as described herein in an appropriate animal model. For example, an agent identified as described herein (e.g., a drug-metabolizing enzyme-modulating agent, an antisense drug-metabolizing enzyme nucleic acid molecule, a drug-metabolizing enzyme-specific antibody, or a drug-metabolizing enzyme-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The drug-metabolizing enzyme proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in the lung. The method involves contacting a biological sample with a compound capable of interacting with the drug-metabolizing enzyme protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered drug-metabolizing enzyme activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the drug-metabolizing enzyme protein in which one or more of the drug-metabolizing enzyme functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and drug-metabolizing enzyme activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in the lung. Accordingly, methods for treatment include the use of the drug-metabolizing enzyme protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the drug-metabolizing enzyme proteins. Antibodies can be prepared from any region of the peptide as described herein. However, preferred regions will include those involved in function/activity and/or drug-metabolizing enzyme/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that drug-metabolizing enzyme proteins of the present invention are expressed in the lung. Specifically, a virtual northern blot shows expression in carcinoid lung. In addition, PCR-based tissue screening panel indicates expression in human and human fetal brain, human bone marrow, human colon, human fetal heart, human fetal liver, human fetal lung, human pancreas, human placenta. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in the lung. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in the lung. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in the lung. Thus, where a specific protein has been correlated with expression in a specific tissue, antibodies that are specific for this protein can be used to identify a tissue type.

The antibodies are also useful for inhibiting protein function, for example, blocking the binding of the drug-metabolizing enzyme peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nucleic acid arrays and similar methods have been developed for antibody arrays.

Nucleic Acid Molecules

The present invention further provides isolated nucleic acid molecules that encode a drug-metabolizing enzyme peptide or protein of the present invention (cDNA, transcript and genomic sequence). Such nucleic acid molecules will consist of, consist essentially of, or comprise a nucleotide sequence that encodes one of the drug-metabolizing enzyme peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences that naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO: 1, transcript sequence and SEQ ID NO: 3, genomic sequence), or any nucleic acid molecule that encodes the protein provided in FIG. 2, SEQ ID NO: 2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO: 1, transcript sequence and SEQ ID NO: 3, genomic sequence), or any nucleic acid molecule that encodes the protein provided in FIG. 2, SEQ ID NO: 2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO: 1, transcript sequence and SEQ ID NO: 3, genomic sequence), or any nucleic acid molecule that encodes the protein provided in FIG. 2, SEQ ID NO: 2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the drug-metabolizing enzyme peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (antisense strand).

The invention further provides nucleic acid molecules that encode fragments of the peptides of the present invention as well as nucleic acid molecules that encode obvious variants of the drug-metabolizing enzyme proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. As indicated by the data presented in FIG. 3, the map position was determined to be on chromosome 6 by ePCR.

FIG. 3 provides information on SNPs that have been identified in a gene encoding the that drug-metabolizing enzyme proteins of the present invention. 4 SNP variants were found, of which all of them beyond ORFs.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6× sodium chloride/sodium citrate (SSC) at about 45C., followed by one or more washes in 0.2×SSC, 0.1% SDS at 50–65C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. 4 SNPs have been identified in the gene encoding the sulfotransferase protein provided by the present invention and are given in FIG. 3.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. As indicated by the data presented in FIG. 3, the map position was determined to be on chromosome 6 by ePCR.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that drug-metabolizing enzyme proteins of the present invention are expressed in the lung. Specifically, a virtual northern blot shows expression in carcinoid lung. In addition, PCR-based tissue screening panel indicates expression in human and human fetal brain, human bone marrow, human colon, human fetal heart, human fetal liver, human fetal lung, human pancreas, human placenta. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in drug-metabolizing enzyme protein expression relative to normal results.

In vitro techniques for detection of mRNA include Northern hybridizations and in situ hybridizations. In vitro techniques for detecting DNA include Southern hybridizations and in situ hybridization.

Probes can be used as a part of a diagnostic test kit for identifying cells or tissues that express a drug-metabolizing enzyme protein, such as by measuring a level of a drug-metabolizing enzyme-encoding nucleic acid in a sample of cells from a subject e.g., mRNA or genomic DNA, or determining if a drug-metabolizing enzyme gene has been mutated. Experimental data as provided in FIG. 1 indicates that drug-metabolizing enzyme proteins of the present invention are expressed in the lung. Specifically, a virtual northern blot shows expression in carcinoid lung. In addition, PCR-based tissue screening panel indicates expression in human and human fetal brain, human bone marrow, human colon, human fetal heart, human fetal liver, human fetal lung, human pancreas, human placenta.

Nucleic acid expression assays are useful for drug screening to identify compounds that modulate drug-metabolizing enzyme nucleic acid expression.

The invention thus provides a method for identifying a compound that can be used to treat a disorder associated with nucleic acid expression of the drug-metabolizing enzyme gene, particularly biological and pathological processes that are mediated by the drug-metabolizing enzyme in cells and tissues that express it. Experimental data as provided in FIG. 1 indicates expression in the lung. The method typically includes assaying the ability of the compound to modulate the expression of the drug-metabolizing enzyme nucleic acid and thus identifying a compound that can be used to treat a disorder characterized by undesired drug-metabolizing enzyme nucleic acid expression. The assays can be performed in cell-based and cell-free systems. Cell-based assays include cells naturally expressing the drug-metabolizing enzyme nucleic acid or recombinant cells genetically engineered to express specific nucleic acid sequences.

Thus, modulators of drug-metabolizing enzyme gene expression can be identified in a method wherein a cell is contacted with a candidate compound and the expression of mRNA determined. The level of expression of drug-metabolizing enzyme mRNA in the presence of the candidate compound is compared to the level of expression of drug-metabolizing enzyme mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate drug-metabolizing enzyme nucleic acid expression in cells and tissues that express the drug-metabolizing enzyme. Experimental data as provided in FIG. 1 indicates that drug-metabolizing enzyme proteins of the present invention are expressed in the lung. Specifically, a virtual northern blot shows expression in carcinoid lung. In addition, PCR-based tissue screening panel indicates expression in human and human fetal brain, human bone marrow, human colon, human fetal heart, human fetal liver, human fetal lung, human pancreas, human placenta. Modulation includes both up-regulation (i.e. activation or agonization) or down-regulation (suppression or antagonization) or nucleic acid expression.

Alternatively, a modulator for drug-metabolizing enzyme nucleic acid expression can be a small molecule or drug identified using the screening assays described herein as long as the drug or small molecule inhibits the drug-metabolizing enzyme nucleic acid expression in the cells and tissues that express the protein. Experimental data as provided in FIG. 1 indicates expression in the lung.

The nucleic acid molecules are also useful for monitoring the effectiveness of modulating compounds on the expression or activity of the drug-metabolizing enzyme gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in drug-metabolizing enzyme nucleic acid expression, and particularly in qualitative changes that lead to pathology. The nucleic acid molecules can be used to detect mutations in drug-metabolizing enzyme genes and gene expression products such as mRNA. The nucleic acid molecules can be used as hybridization probes to detect naturally occurring genetic mutations in the drug-metabolizing enzyme gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the drug-metabolizing enzyme gene associated with a dysfunction provides a diagnostic tool for an active disease or susceptibility to disease when the disease results from overexpression, underexpression, or altered expression of a drug-metabolizing enzyme protein.

Individuals carrying mutations in the drug-metabolizing enzyme gene can be detected at the nucleic acid level by a variety of techniques. FIG. 3 provides information on SNPs that have been identified in a gene encoding the that drug-metabolizing enzyme proteins of the present invention. 4 SNP variants were found, of which all of them beyond ORFs. As indicated by the data presented in FIG. 3, the map position was determined to be on chromosome 6 by ePCR. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a drug-metabolizing enzyme gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant drug-metabolizing enzyme gene and a wild-type gene can be determined by direct DNA sequencing. A variety of automated sequencing procedures can be utilized when performing the diagnostic assays (Naeve, C. W., (1995) Biotechniques 19:448), including sequencing by mass spectrometry (see, e.g., PCT International Publication No. WO 94/16101; Cohen et al., Adv. Chromatogr. 36:127–162 (1996); and Griffin et al., Appl. Biochem. Biotechnol. 38:147–159 (1993)).

Other methods for detecting mutations in the gene include methods in which protection from cleavage agents is used to detect mismatched bases in RNA/RNA or RNA/DNA duplexes (Myers et al., Science 230:1242 (1985)); Cotton et al., PNAS 85:4397 (1988); Saleeba et al., Meth. Enzymol. 217:286–295 (1992)), electrophoretic mobility of mutant and wild type nucleic acid is compared (Orita et al., PNAS 86:2766 (1989); Cotton et al, Mutat. Res. 285:125–144 (1993); and Hayashi et al., Genet. Anal. Tech. Appl. 9:73–79 (1992)), and movement of mutant or wild-type fragments in polyacrylamide gels containing a gradient of denaturant is assayed using denaturing gradient gel electrophoresis (Myers et al., Nature 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the drug-metabolizing enzyme gene in an individual in order to select an appropriate compound or dosage regimen for treatment. FIG. 3 provides information on SNPs that have been identified in a gene encoding the that drug-metabolizing enzyme proteins of the present invention. 4 SNP variants were found, of which all of them beyond ORFs.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control drug-metabolizing enzyme gene expression in cells, tissues, and organisms. A DNA antisense nucleic acid molecule is designed to be complementary to a region of the gene involved in transcription, preventing transcription and hence production of drug-metabolizing enzyme protein. An antisense RNA or DNA nucleic acid molecule would hybridize to the mRNA and thus block translation of mRNA into drug-metabolizing enzyme protein.

Alternatively, a class of antisense molecules can be used to inactivate mRNA in order to decrease expression of drug-metabolizing enzyme nucleic acid. Accordingly, these molecules can treat a disorder characterized by abnormal or undesired drug-metabolizing enzyme nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the drug-metabolizing enzyme protein, such as substrate binding.

The nucleic acid molecules also provide vectors for gene therapy in patients containing cells that are aberrant in drug-metabolizing enzyme gene expression. Thus, recombinant cells, which include the patient's cells that have been engineered ex vivo and returned to the patient, are introduced into an individual where the cells produce the desired drug-metabolizing enzyme protein to treat the individual.

The invention also encompasses kits for detecting the presence of a drug-metabolizing enzyme nucleic acid in a biological sample. Experimental data as provided in FIG. 1 indicates that drug-metabolizing enzyme proteins of the present invention are expressed in the lung. Specifically, a virtual northern blot shows expression in carcinoid lung. In addition, PCR-based tissue screening panel indicates expression in human and human fetal brain, human bone marrow, human colon, human fetal heart, human fetal liver, human fetal lung, human pancreas, human placenta. For example, the kit can comprise reagents such as a labeled or labelable nucleic acid or agent capable of detecting drug-metabolizing enzyme nucleic acid in a biological sample; means for determining the amount of drug-metabolizing enzyme nucleic acid in the sample; and means for comparing the amount of drug-metabolizing enzyme nucleic acid in the sample with a standard. The compound or agent can be packaged in a suitable container. The kit can further comprise instructions for using the kit to detect drug-metabolizing enzyme protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS: 1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides that cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the drug-metabolizing enzyme proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the drug-metabolizing enzyme gene of the present invention. FIG. 3 provides information on SNPs that have been identified in a gene encoding the that drug-metabolizing enzyme proteins of the present invention. 4 SNP variants were found, of which all of them beyond ORFs.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified drug-metabolizing enzyme gene of the present invention can be routinely identified using the sequence information disclosed herein can be readily incorporated into one of the established kit formats which are well known in the art, particularly expression arrays.

Vectors/Host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual.* 2nd. ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual.* 2nd. ed., Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli*, Streptomyces, and *Salmonella typhimurium*. Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterokinase. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990) 119–128). Alternatively, the sequence of the nucleic acid molecule of interest can be altered to provide preferential codon usage for a specific host cell, for example *E. coli*. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kurjan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf 9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual.* 2nd, ed., Cold Spring Harbor Laboratory, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, appropriate secretion signals are incorporated into the vector. The signal sequence can be endogenous to the peptides or heterologous to these peptides.

Where the peptide is not secreted into the medium, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a drug-metabolizing enzyme protein or peptide that can be further purified to produce desired amounts of drug-metabolizing enzyme protein or fragments. Thus, host cells containing expression vectors are useful for peptide production.

Host cells are also useful for conducting cell-based assays involving the drug-metabolizing enzyme protein or drug-metabolizing enzyme protein fragments, such as those described above as well as other formats known in the art. Thus, a recombinant host cell expressing a native drug-metabolizing enzyme protein is useful for assaying compounds that stimulate or inhibit drug-metabolizing enzyme protein function.

Host cells are also useful for identifying drug-metabolizing enzyme protein mutants in which these functions are affected. If the mutants naturally occur and give rise to a pathology, host cells containing the mutations are useful to assay compounds that have a desired effect on the mutant drug-metabolizing enzyme protein (for example, stimulating or inhibiting function) which may not be indicated by their effect on the native drug-metabolizing enzyme protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a drug-metabolizing enzyme protein and identifying and evaluating modulators of drug-metabolizing enzyme protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the drug-metabolizing enzyme protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence(s) can be operably linked to the transgene to direct expression of the drug-metabolizing enzyme protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, drug-metabolizing enzyme protein activation, and signal transduction, may not be evident from in vitro cell-free or cell-based assays. Accordingly, it is useful to provide non-human transgenic animals to assay in vivo drug-metabolizing enzyme protein function, including substrate interaction, the effect of specific mutant drug-metabolizing enzyme proteins on drug-metabolizing enzyme protein function and substrate interaction, and the effect of chimeric drug-metabolizing enzyme proteins. It is also possible to assess the effect of null mutations, that is mutations that substantially or completely eliminate one or more drug-metabolizing enzyme protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated polypeptide having an amino acid sequence consisting of SEQ ID NO:2.

2. An isolated polypeptide having an amino acid sequence comprising SEQ ID NO:2.

3. A composition comprising the polypeptide of claim 1 and a carrier.

4. A composition comprising the polypeptide of claim 2 and a carrier.

5. An isolated polypeptide having an amino acid sequence that is 95% identical with SEQ ID NO:2.

6. A composition comprising the polypeptide of claim 5 and a carrier.

* * * * *